US00PP23385P3

(12) United States Plant Patent
Dirr

(10) Patent No.: US PP23,385 P3
(45) Date of Patent: Feb. 12, 2013

(54) ***VIBURNUM* PLANT NAME 'PIIVIB-I'**

(50) Latin Name: ***Viburnum* sp. L.**
Varietal Denomination: PIIVIB-I

(75) Inventor: Michael A. Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 110 days.

(21) Appl. No.: 13/068,272

(22) Filed: May 6, 2011

(65) Prior Publication Data

US 2012/0284887 P1 Nov. 8, 2012

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Plant Introductions, Inc.—promotional page from Plant Introductions website showing color picture of Viburnam-02 which is Viburnam Plant Named 'PIIVIB-I. (Downloaded May 5, 2011.).

*Primary Examiner* — June Hwu
(74) *Attorney, Agent, or Firm* — Greenlee Sullivan P.C.

(57) ABSTRACT

A new and distinct cultivar of *Viburnum* plant named 'PIIVIB-I', characterized by its compact, mounding growth habit, small, lustrous, dark green, evergreen foliage, white flowers produced in abundance even on young plants, clusters of red fruit that turn black when mature.

4 Drawing Sheets

Genus and species of plant claimed: *Viburnum* sp. L.
Variety denomination: 'PIIVIB-I'.

BACKGROUND OF THE INVENTION

The present invention relates to a new and distinct cultivar of *Viburnum,* a member of the Adoxaceae family, hereinafter referred to by its cultivar name 'PIIVIB-I'. This cultivar is grown primarily as an ornamental for landscape use.

The cultivar originated from an open-pollination of *Viburnum* 'Nantucket' (unpatented) in Watkinsville, Ga., and was selected from the progeny of this pollination by continued evaluation for compact growth habit and improved evergreen leaf and flower characteristics.

'PIIVIB-I' has been asexually reproduced by semi-hardwood cuttings in Watkinsville, Ga. since 2006. The characteristics of the cultivar have been stable and reproduced true-to-type in successive vegetative generations.

SUMMARY OF THE INVENTION

'PIIVIB-I' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIVIB-I' from all other varieties in commerce known to the inventor. 1) Compact, mounding growth habit. 2) Small, lustrous, dark green, evergreen foliage. 3) White flowers produced in abundance even on young plants. 4) Clusters of red fruit that turn black when mature.

'PIIVIB-I' is distinguished from its female parent 'Nantucket' by its growth habit and foliage. 'PIIVIB-I' has a compact, mounding growth habit and small, dark green, evergreen foliage that is lustrous on the upper surface and pubescent on the lower surface, whereas 'Nantucket' has a compact, upright growth habit and larger, semi-evergreen foliage that is pubescent on the upper and lower surfaces. There are no other cultivars of *Viburnum* with this combination of characteristics known to the inventor.

Plants of the new *Viburnum* can be compared to plants of the cultivar 'Conoy' (unpatented), although 'PIIVIB-I' is distinguished from 'Conoy' by growth habit and foliage and flower characteristics. 'PIIVIB-I' has a compact, mounding growth habit, small, dark green, evergreen foliage, and white flowers produced in abundance even on young plants, whereas 'Conoy' has a compact, irregular growth habit, smaller, slightly twisted, evergreen foliage, and less abundant, smaller inflorescences.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Viburnum.*

DETAILED DESCRIPTION

Figure 1:
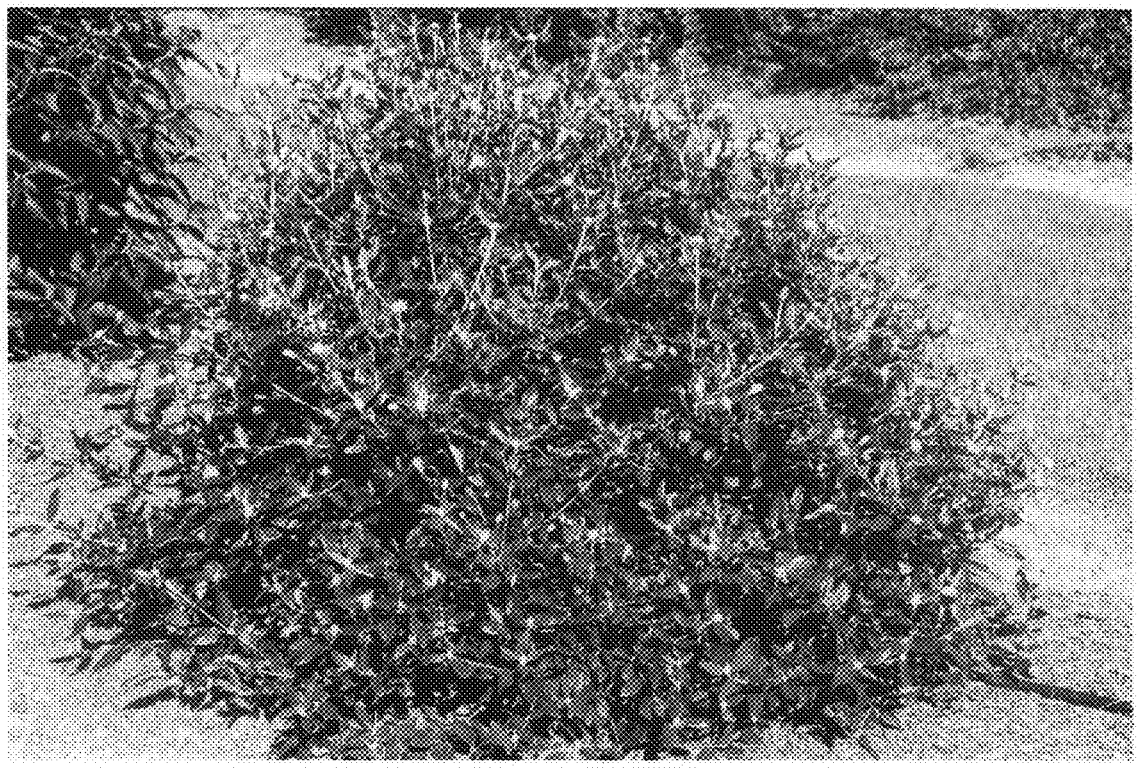
FIG. 1 shows the growth habit of the original five-year-old plant of 'PIIVIB-I'.
Figure 2:
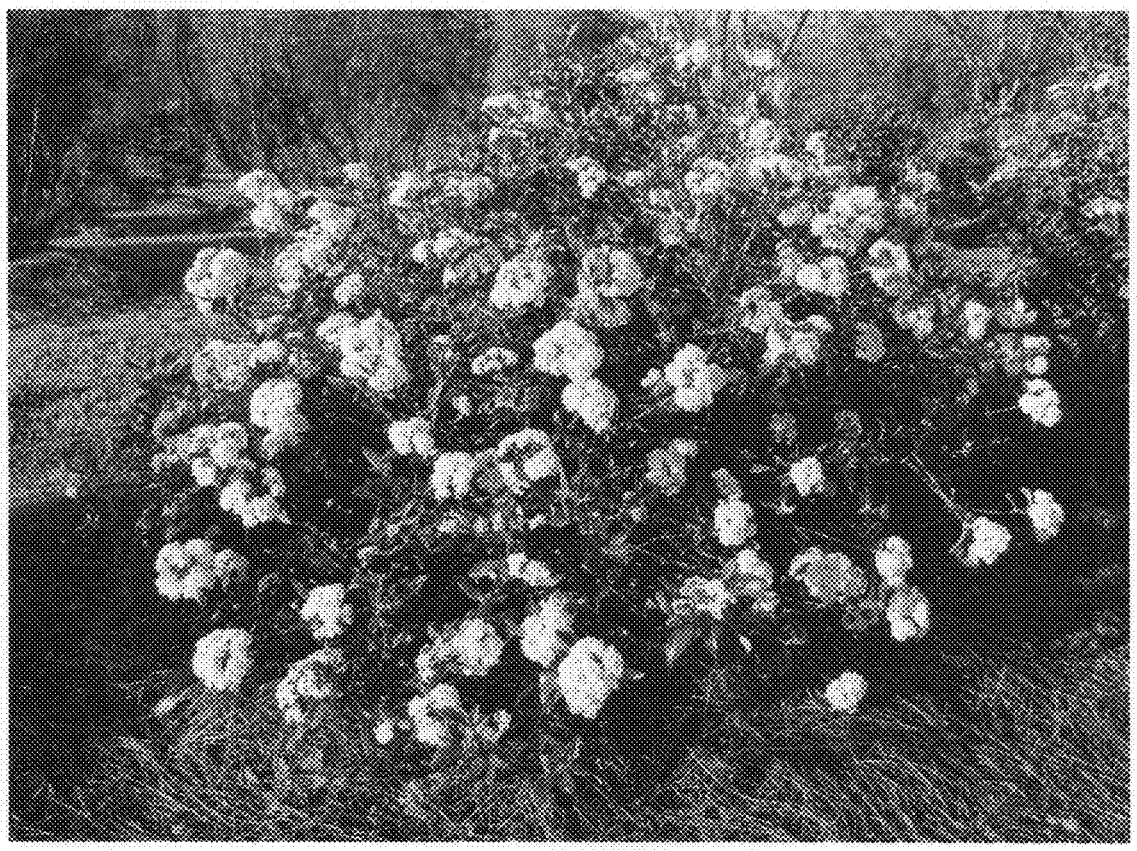
FIG. 2 shows 'PIIVIB-I' in flower.
Figure 3:
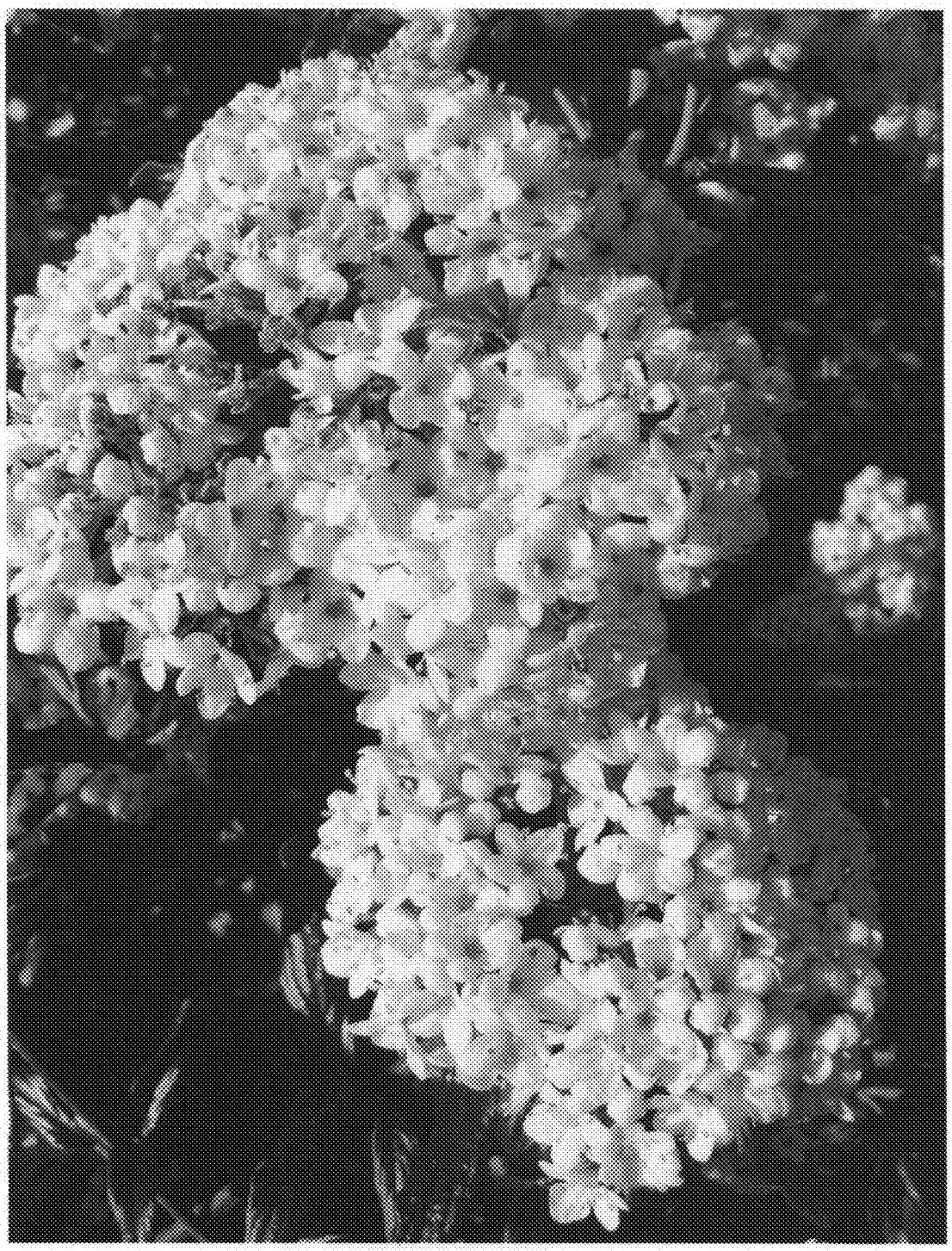
FIG. 3 shows a close-up of the flowers of 'PIIVIB-I'.
Figure 4:
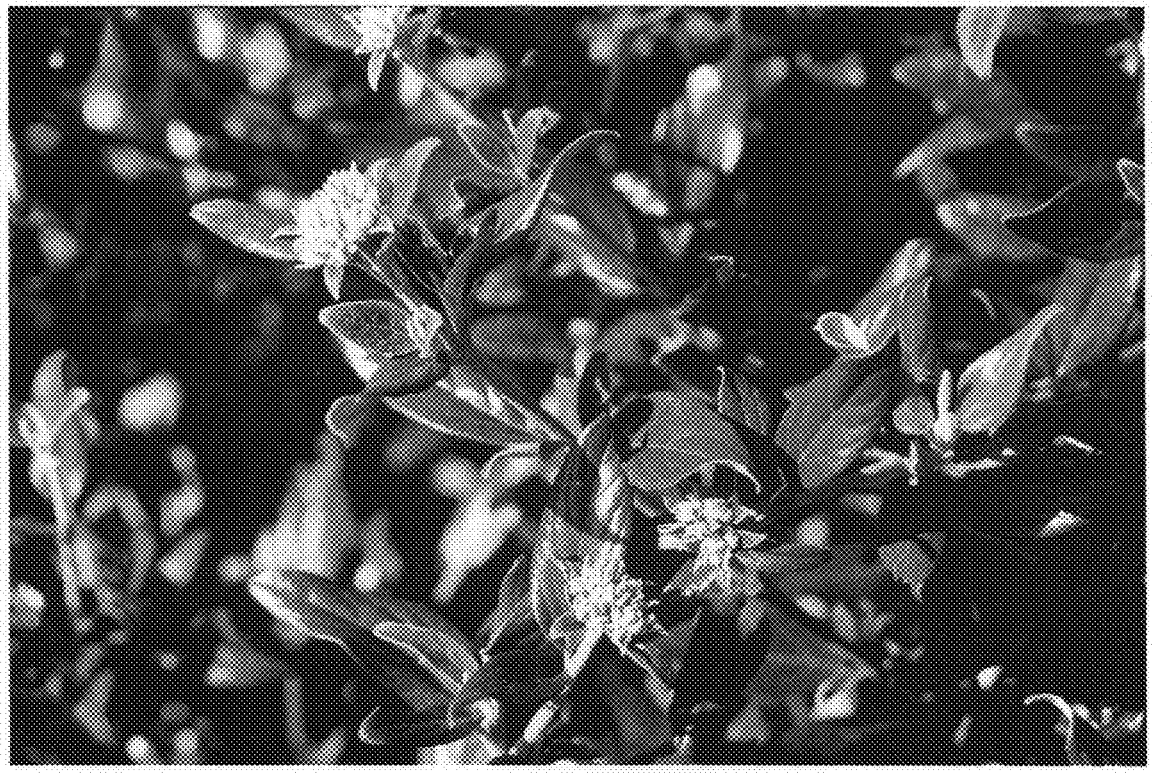
FIG. 4 shows a close-up of the foliage and flower buds of 'PIIVIB-I'.

In the following description, color references are made to The Royal Horticultural Society Colour Chart, 2001 Edition, except where general terms of ordinary dictionary significance are used. Plants used for the description were grown in 11.8 L containers in full sun under outdoor conditions in a nursery in Watkinsville, Ga.

Botanical classification: 'PIIVIB-I' is a cultivar of *Viburnum*.

Parentage: The current variety is a progeny from an open-pollination of *Viburnum* 'Nantucket'.

Propagation: Vegetatively by stem cuttings.

Time to initiate roots in summer: About 5 to 6 weeks at 32° C.

Plant description: The claimed variety is a freely branching, compact, mounding evergreen shrub. The plant is hardy in USDA Zones 6 to 8.

*Root description.*—Numerous, fleshy, and well-branched.

*Plant height.*—About 140 cm after five years. Plant width: about 213 cm after five years.

*Stems.*—First year stems have a diameter of about 3 mm, a rounded shape, and stellate pubescence. The stem color is 193B, maturing to 144A. Second year stems have a diameter of about 5 mm and color is 165A.

*Internode length.*—About 3.5 cm.

*Vegetative buds.*—Arrangement: opposite. Shape: valvate. Pubescence: stellate. Size: about 5 mm in length, about 2 mm in width; Color: 157B on young stems, and 165D on mature stems.

Foliage description:

*Arrangement.*—Opposite. Length: about 5.8 cm. Width: about 2.3 cm.

*Shape.*—Lanceolate to elliptical. Apex: acute. Base: rounded to oblique. Margin: entire, often undulating.

*Texture.*—Glabrous, lustrous above, stellate pubescence below.

*Venation.*—Pinnate. Venation color: 147A.

*Color of emerging leaves.*—144A on the upper surface, and 193B on the lower surface. Color of mature leaves: on the upper surface is 147A, and 195B on the lower surface.

*Petiole length.*—About 1 cm. Petiole diameter: about 1 mm. Pubescence: stellate. Petiole color: 193B.

Flower description:

*Flower type and arrangement.*—Inflorescence is a terminal cyme about 9 cm in diameter and 4 cm high. Flower buds are formed on previous season's growth and are present from summer until they open the following spring. An inflorescence contains about 175 individual flowers. Individual flowers retain their color and are showy for about 1 week. Flowers are self cleaning. Individual flowers in an inflorescence open over a period of about 1 week. Therefore, an inflorescence is showy for about 2 weeks. Bloom period: spring (mid April in Watkinsville, Ga.). Fragrance: slight sweet odor.

*Flower bud diameter.*—About 3 mm. Flower bud length: about 5 mm. Flower bud shape: oval to oblong. Flower bud color: 155D. Pubescence: stellate.

*Flower diameter.*—About 1 cm. Flower height: about 6 mm.

*Pedicels.*—About 3 mm in length, about 1 mm in width, with stellate pubescence, and 195B in color.

*Peduncle.*—About 2.7 cm in length, about 2 mm in width, with stellate pubescence, and 195B in color.

Petals:

*Quantity.*—5 petals per flower.

*Petal length.*—About 6 mm. Petal width: about 5 mm.

*Petal shape.*—Elliptical, with obtuse to rounded apex, cuneate to acute base, and entire margin. Petal texture: smooth with no pubescence.

*Petal color.*—At peak bloom the upper and lower surfaces are 155C.

Stamens:

*Quantity.*—5 per flower.

*Anthers.*—About 1 mm in length and about 1 mm in width, and 10B in color.

*Filaments.*—About 2 mm in length and less than 1 mm in width, and 155C in color.

*Pollen.*—Produced in moderate quantities per flower, and 10B in color.

Pistils:

*Quantity/arrangement.*—1 per flower, superior.

*Pistil length.*—About 3 mm.

*Pistil width.*—About 1 mm.

*Pistil color.*—144C in color.

*Stigma.*—Usually 1 per pistil, round in shape and 178A in color.

*Style.*—About 1 mm in length and width, round in shape, and 144C in color.

*Ovary.*—1 per flower, about 2 mm in height and about 1 mm in width, and 144C in color.

Fruit:

*Type/appearance.*—Drupe, oblong to oval-rounded in shape, held in clusters.

*Fruit length.*—About 7 mm.

*Fruit diameter.*—About 6 mm.

*Fruit color.*—46A when immature changing to 202A at maturity.

*Seeds.*—About 6 mm in length, about 5 mm in width, 165C in color, and each drupe contains 1 seed.

Disease/pest resistance: No specific pest or disease susceptibility has been observed.

I claim:

1. A new and distinct *Viburnum* plant named 'PIIVIB-I', substantially as illustrated and described herein.

* * * * *